United States Patent [19]

Mayers et al.

[11] Patent Number: 5,393,737
[45] Date of Patent: Feb. 28, 1995

[54] CYTOTOXIC DRUG CONJUGATES FOR TREATMENT OF NEOPLASTIC DISEASES

[75] Inventors: George L. Mayers, Olcott, N.Y.; Jafar Razeq, Ramallah, Israel; Mahmoud M. Abu-Hadid, Lakawanna, N.Y.

[73] Assignee: Health Research, Inc., Buffalo, N.Y.

[21] Appl. No.: 932,660

[22] Filed: Aug. 20, 1992

[51] Int. Cl.$^6$ .................. A61K 37/02; A61K 37/36; C07K 13/00
[52] U.S. Cl. .................. 514/12; 514/21; 514/23; 530/326; 530/394; 530/399; 530/351; 424/85.1; 536/6.4; 536/18.7; 536/112; 536/27.13; 536/114
[58] Field of Search .................. 514/12, 21, 23; 530/394, 326, 399, 351; 424/85.1; 536/18.7, 112, 24, 6.4

[56] References Cited

U.S. PATENT DOCUMENTS

| | | | |
|---|---|---|---|
| 5,057,301 | 10/1991 | Wilbur et al. | 530/395 |
| 5,087,616 | 2/1992 | Myers et al. | 514/21 |
| 5,094,848 | 3/1992 | Brixner | 530/345 |

OTHER PUBLICATIONS

Abu-hadid, M. M., et al. Selective elimination of idiotype-binding cells in vivo by a drug-idiotype conjugate demonstrates the functional significance of these cells in immune regulation, Proc. Natl. Acad. Sci. USA 85:3990–3994, 1988.

Flanagan, P. A. et al., Evaluation of protein-N-(2-hydropropyl)methacrylamide copolymer conjugates as targetable drug carriers. 1. Binding, pinocytic uptake and intracellular distribution of transferrin and anti-transferrin receptor antibody conjugates. Biochim. Biophys. Biophys. Acta 993:83–91, 1989.

Kornfeld, S. B., et al., Assessment of Ligand Effects in Intracellular Transfficking of Ricin A Chain Anti-Ricin Hybridomas. Cancer Res. 51:1689–1693, 1991.

O'Keefe, et al., Two pathways of transferrin recycling evident in a variant of mouse LMTK cells. Somatic Cell Molec. Genet. 14:473–487, 1988.

Colombatti, M., et al., Sensitivity of human glioma cells to cytotoxic heteroconjugates. Int. J. Cancer 42:441–448, 1988.

Arnon, R., et al., In vitro and in vivo efficacy of conjugates of Daunomycin with anti-tumor antiboies. Immunol. Rev. 62:5–27, 1982.

Hurwitz, E., et al., The covalent linking of two nucleotide analogues to antibodies. J. Med. Chem. 28:137–140, 1985.

Johnson, V. G., et al., Improved tumor-specific immunotoxins in the treatment of CNS and leptomeningeal neoplasia. J. Neurosurg. 70:240–248, 1989.

Batra, J. K., et al., I. Single-chain immunotoxins directed at the human transferrin receptor containing Pserdomonas exotoxin A or diptheria toxin: Anti--TFR(Fv)-PE40 and DT388-anti-TFR(Fv). Mol. Cell. Biol. 11:2200–2205, 1991.

Bergamaschi, G., et al., Killing of K562 cells with conjugates between human transferrin and a ribosome-inactivating protein (SO-6). Br. J. Haemat. 68:379–384, 1988.

Cazzola, M., et al., Cytotoxic activity of an anti-transferrin receptor immunotoxin on normal and leukemic human hematopoietic progenitors. Cancer Res. 51:536–541, 1991.

(List continued on next page.)

Primary Examiner—Ronald W. Griffin
Attorney, Agent, or Firm—Michael L. Dunn; James F. Mudd

[57] ABSTRACT

A novel composition of matter comprising a ligand-carbohydrate-cytotoxic drug conjugate is produced by the steps of (1) reacting a carbohydrate with a ligand, (2) reacting the product of step (1) with a cytotoxic drug, and (3) stabilizing the product of step (2) by reduction. The composition is used for treating a neoplastic disease by a process of administering a non-toxic, effective amount of a ligand-carbohydrate-cytotoxic drug conjugate to a human being or animal in need of such a treatment.

48 Claims, 12 Drawing Sheets

OTHER PUBLICATIONS

Yeh, C-J. G., et al., Killing of human tumor cells in culture with adriamycin conjugates of human transferrin. Clin. Immunol. Immunopath. 32:1–11, 1984.

Faulk, W. P., Taylor, C. G., Yeh, C-J. G., McIntryre, J. A. Preliminary clinical study of transferrin-Adriamycin conjugate for drug delivery to acute leukemia patients. Mol. Biother. 2:57–60, 1990.

Sela, M., et al., Conjugates of antibodies with cytotoxic drugs. In immunoconjugates. Antibody Conjugates in Radioimaging and Therapy of Cancer (C.-W. Vogel, editor). New York, Oxford University Press pp. 189–216 (1987).

Raso, v., Mediation of toxin entry into cells via naturally occurring ligand receptor sites, In Immuno—conjugates. Antibody Conjugates in Radioimaging and Therapy of Cancer (C.—W.-Vogel, editor). New York, Oxford University Press, pp. 116–152 (1987).

Goldenberg, D. M., Targeted cancer treatment, Immunology Today, vol. 10, No. 9, pp. 286–288 (1989).

Davies, A. J. S. et al., Drug targeting: Introduction. Cancer Surveys, vol. 1 No. 3, pp. 347–353 (1982).

Garnett, M. C. et al., 608th Meeting, Keelf, Cancer Research Campaign Laboratories, Univ. of Nottingham, pp. 1035–1036 (1984).

Sezaki, H., et al., Macromolecule-drug conjugates in targeted cancer chemotherapy, CRC Critical Reviews in Therapeutic Drug Carrier Systems, vol. 1, Issue 1, pp. 1–38 (1984).

CYTOTOXIC DRUG CONJUGATES FOR TREATMENT OF NEOPLASTIC DISEASES

This invention was made in part under grant number CA 35329 from the National Cancer Institute and grant number DMB87-15954 from the National Science Foundation. The United States Government may have certain rights in this invention.

BACKGROUND OF THE INVENTION

This invention relates to new chemotherapeutic drugs for the treatment of neoplastic diseases. Successful cancer chemotherapy requires selective elimination of neoplastic cells both at the primary site and distant metastases. Most drug protocols attempt to exploit the growth characteristics of transformed cells that usually centers on loss of regulated growth. Thus, most chemotherapeutic agents selectively attack dividing cells both neoplastic and normal, and doses that are adequate to eliminate the cancerous tissues usually annihilate the host. To limit the detrimental effects of the drugs, administration of cytotoxic agents has been controlled to effect extensive destruction of the neoplastic cells while allowing the affected normal cells to recover. Oncologists, who regularly walk this tightrope, often observe that the therapy eventually fails to control the cancer. To overcome the inadequacies of standard drug therapy, efforts are made to more effectively target the drugs specifically to the cells of interest. The most general approach is to try to infuse the drugs directly into the tumor tissue so as to maintain high drug concentrations in the vicinity of tumor cells and somewhat lower concentrations elsewhere to control the detrimental effects to normal tissues. A second approach is to attempt to target the drugs directly to the tumor cells to maintain a high localized level of drug. Although considerations of this approach date back to the turn of the century when it was first suggested by Paul Ehrlich, as reported by R. Arnon and M. Sela in Immunological Rev. (1982) Vol. 62, page 5, little practical success has been achieved. The development of monoclonal antibodies in the mid-seventies reinvigorated these programs since specifically tailored antibodies could be developed in unlimited supply for use in targeting such agents which have become commonly referred to as "Magic Bullets".

Although the application of monoclonal antibodies for directing drugs and toxins to neoplastic cells was anticipated to result in major breakthroughs in cancer chemotherapy, it has produced limited success. There are many problems that this form of therapy must overcome.

The purpose of this invention is to provide novel compositions that overcome problems of the past by limiting the detrimental effects of drugs on normal cells, while destroying neoplastic cells.

SUMMARY OF THE INVENTION

The foregoing purposes are achieved by providing compositions of matter comprising ligand-carbohydrate-cytotoxic drug conjugates, such compositions also known herein as toxogens, and processes for producing such compositions.

The compositions are useful for treating neoplastic diseases or autoimmunities, or allergies or any condition that requires elimination of specific cell populations that express an addressible receptor; by processes comprising administering a nontoxic, effective amount of the conjugates of the invention to a human being or animal in need of such treatment.

DESCRIPTION OF THE PREFERRED EMBODIMENTS

The ligand-carbohydrate-cytotoxic drug conjugates of the invention are prepared by the steps comprising:

(1) reacting a carbohydrate compound with a ligand to produce a Schiff base, (2) reacting the product of step (1) with a cytotoxic drug and (3) stabilizing the product of step (2) by reduction to produce the conjugates of the invention.

Suitable ligands include but are not limited to cytokines and growth factors such as transferrin, epidermal growth factor, granulocyte macrophage - colony stimulating factor (GM-CSF), and the like. The choice of ligand is dictated by the repertoire of receptors expressed by the cell population to be eliminated and limited by any detrimental effects of the particular toxogen on the host. A preferred ligand for many T-leukemic cells is iron-saturated human transferrin. The source of this ligand is purification from human serum and can be purchased from many biological supply companies. In many situations where isolation of a particular ligand is difficult, recombinant proteins are available.

Suitable carbohydrates include various polysaccharide compositions, preferably, that are highly branched and contain a large number of 1,2-diols (adjacent hydroxyl groups on a monomer unit) or 1,2-aminohydroxyl groups (adjacent amino and hydroxyl groups on a monomer unit). Examples of suitable carbohydrates include various gums such as gum arabic or gum tragacanth and high molecular weight polysaccharides such as dextran B 1355S. The carbohydrates are preferably oxidized prior to reaction to make the conjugates of the invention.

The carbohydrates generally have a molecular weight in the range above about 50,000, preferably about 75,000 up to about 40 million. The carbohydrates should be highly branched.

Specific useful polysaccharides include gum arabic. More preferred is oxidized gum arabic. Typically, aldehyde functional groups are introduced into gum arabic by oxidation with an oxidizing agent such as sodium periodate. The reaction is incubated for a number of hours.

The unreacted periodate and other small reaction products are removed by overnight dialysis against phosphate buffer.

Since the polysaccharides are required to carry a reasonable number of cytotoxic molecules and must withstand fragmentation or oxidation with periodate, the polysaccharides should have a number of monomer units with cisdiols, or 1,2 amino-hydroxy groups, and they should be highly branched. Other compounds with adjacent hydroxyl groups, 2,3—, 3,4—, 4,5— and 5,6-dihydroxyl groups or other compounds with adjacent amino-hydroxy groups, 2,3—, 3,4—, 4,5—, 5,6—, 3,2—, 4,3—, 5,4—, 6,5— amino-hydroxyl groups can be employed.

Suitable cytotoxic drugs include members of the following groups or families:

1) nitrogen - mustard types, such as melphalan;
2) anthracyclines such as adriamycin, also known as doxorubicin, and daunomycin;
3) nucleoside analogues, such as cytosine arabinoside, also known as araC or 1-beta-D-arabinofuranosylcytosine or cytarabine;
4) antimetabolites, such as methotrexate.

Preferred examples of cytotoxic drugs include:
melphalan
methotrexate
adriamycin, and
cytosine arabinoside The conjugates of the invention preferably contain about 2 to about 5 molecules of the ligand and several hundred molecules of the drug per molecule of carbohydrate. The more general ranges include 1 to about 20 molecules of ligand per mole of carbohydrate, and at least about 100 molecules of drug per mole of carbohydrate. The preferred range is about 100 to about 20,000 molecules of drug per mole of carbohydrate, more particularly, about 100 to about 2,000 moles of drug per mol of carbohydrate.

The components are generally reacted at room temperature and for times in the range of one to several hours.

A high ratio of about 50,000 to about 100,000 moles of drug is employed per mole of carbohydrate to produce toxogens with a high content of the cytotoxic drug essential for effective therapy. About 2 to 5 moles of ligand is employed per mole of carbohydrate.

In the reaction to form the conjugates, the polysaccharides are oxidized to cleave the carbon-carbon bond between the hydroxyl groups or amino-hydroxyl groups to form dialdehydes. The dialdehyde compositions are mixed with the ligand at a pH in the range of about 3 to about 11, preferably a pH of about 8 to start the coupling reaction of the components.

After mixing the foregoing components for about 15 minutes, the drug is added and coupling continues to provide an intermediate conjugate. The intermediate conjugates are capable of reverting back to the original components. Therefore, stabilizers such as sodium borohydride are added in an effective stabilizing amount to stabilize the conjugate. Other stabilizers include reducing agents such as sodium cyano borohydride. The stabilizer hydrogenates the intermediate conjugate to produce the final conjugate. Depending on the ligand and drug, conjugation chemistry can be modified to provide a viable product. For example, melphalan may not provide an effective reagent when directly coupled via the amino group. Conjugation of melphalan through its carboxyl group has been found to produce a conjugate that can release the cytotoxic agent. To prepare such a conjugate the oxidized polysaccharide is allowed to react with the ligand and 15 minutes later with ethylenediamine. This conjugate is stabilized by reduction with sodium borohydride. N-acetyl melphalan N-hydroxysuccinimide ester, prepared by acetylation of melphalan and activation of the carboxyl group by N-hydroxysuccinimide and dicyclohexycarbodiimide, is allowed to react with the ligand-carbohydrate-ethylenediamine conjugate to produce a ligand-carbohydrate-ethylenediamine-melphalan conjugate.

The conjugates of the invention, also called toxogens, are normally solid at room temperature, but are generally maintained in aqueous solution with a pH of about 3 to 11, preferably about 8 with the aid of a buffer solution such as an acetate buffer which provides a pH of about 3.6 to 5.6, a borate buffer which provides a pH of about 7.5 to 10.1, and a phosphate buffer which provides a pH of about 6.9 to 8.0.

Uses of the conjugates or toxogens of the invention are described herein as follows:

Treatment of T-leukemic cells in vitro with a transferringum arabic-araC conjugate: The human T-cell leukemia cell line, CCRF-CEM, that has been shown to express functional transferrin receptors was tested with the transferrin-gum arabic-drug conjugate. Five ml of cells, $5 \times 10^5$ tumor cells per ml, were treated with various concentrations between 2 and 200 μg/ml of the toxogen for 72 hrs. The effect of the toxogen on the cell populations was determined from a cell count using trypan blue exclusion.

In vivo treatment of AKR mice with a transferrin-gum arabic-araC conjugate: Mice were inoculated subcutaneously with $1 \times 10^6$ SL-2 T-cell leukemia cells that were freshly transferred from tumor bearing mice, and then treated with the toxogen either intravenously or intratumorally. The in vivo regimen, which was usually given 2 and 72 hours after injection of the tumor cells, was 0.5 mg (0.2 ml) of the toxogen injected intravenously into the tail vein. In addition, a group of mice that was treated intravenously had been challenged with $1 \times 10^7$ SL-2 cells. Control groups that received either $1 \times 10^6$ or $1 \times 10^7$ SL-2 cells were given no treatment. There was also a control group that received $1 \times 10^6$ SL-2 cells and that was given intravenously an amount of gum arabic-araC equivalent to the toxogen. To evaluate if targeted therapy could still be effective after the tumor cells had engrafted, groups of mice were given either $3 \times 10^5$ or $1 \times 10^6$ tumor cells. After 72 hours, the mice were treated with the drug-conjugate and then received either one more injection on day four or 6 additional injections on the next 6 consecutive days. Control mice for each dose of tumor cells received no conjugate.

Immunohistochemistry to identify infiltrating neoplastic T cells: Mice, with or without tumor engraftment, were each injected intraperitoneally with 0.5 ml of a solution of bromodeoxyuridine (BUdR) (10 mg/ml) and sacrificed one hour later. The spleens, lungs and livers were removed, sectioned and fixed in 70% cold ethanol for 48 hours followed by paraffin embedding. Following treatment with 3% $H_2O_2$ in methanol to block endogenous peroxidase activity, thin sections on cover slips were dipped in 4N HCl for 20 minutes at room temperature to partially denature the DNA. The presence of BUdR incorporation was detected using anti-BUdR antibody (3D9) and an immunoperoxidase procedure (Vectastain ABC kit). Diaminobenzidine was used as the substrate for labeling, and samples were finally counterstained with hematoxylin.

The following examples are intended to illustrate the invention but not to limit it. Unless noted otherwise, all parts are by weight and all temperatures are given in degrees Celsius.

A typical preparation of a conjugate of the invention is described in the following illustrative example:

EXAMPLE 1

(A) An oxidized polysaccharide was prepared by oxidizing gum arabic with sodium periodate. 10 ml of a solution containing 0.1 gram of gum arabic was mixed with 10 ml of 0.2 molar sodium periodate at 4° C. The reaction was incubated for 48 hours. The unreacted periodate and other small reaction products were removed by overnight dialysis against phosphate buffer.

(B) To 1.0 ml of the oxidized polysaccharide prepared as in Example 1 (A), 0.5 ml of iron-saturated human transferrin (5.0 mgs/ml) was added, and the pH of the solution was maintained at 8.0 with NaOH. After the mixture had stirred for 15 minutes at room temperature, 24 mgs of araC trace labeled with ($^3$H)araC were added for each mg of the polysaccharide, and the pH of the reaction mixture was adjusted to 8.0. Tritiated araC was used to calculate the number of drug molecules being attached to the polysaccharide. The reaction was allowed to continue for two hours at room temperature while maintaining the pH at 8.0. Reactants were reduced with 2.0 M sodium borohydride (0.0375 mg/0.5 ml $H_2O$) for one hour at room temperature. The uncoupled araC was removed by overnight dialysis against borate buffered saline (BBS) at a pH of 8.0. The toxogen transferrin-gum arabic-araC was stored at 4° C.

A number of different preparations of the transferrin-gum arabic-drug conjugate have been made. The conditions and results of typical preparations are shown in Table 1.

In general, the number of araC molecules that were attached to the polysaccharide was in the range shown in Table 1. The useful range for treatment of neoplastic disease is about 100 to 250. Based on the extinction coefficient for diferric transferrin ($E^{1\%}_{280} = 14.1[12]$), it was calculated that 1 to 2 transferrin molecules had been attached to each unit of carbohydrate.

EXAMPLE 2

In vitro cytotoxicity of transferrin-gum arabic-araC drug conjugate: The transferrin-gum arabic-araC drug conjugate prepared as in Example 1B, was tested on the human T leukemic cell line CCRF-CEM that expresses a transferrin receptor which has been shown to induce proliferation. CCRF-CEM cells were

TABLE 1

PREPARATIONS OF GUM ARABIC-ARAC CONJUGATES AND THE EFFECTS OF THE REACTION CONDITIONS ON THE NUMBER OF DRUG MOLECULES ATTACHED.

| AraC M | Oxidized Gum Arabic M | Reaction pH | No. of AraC per Gum Arabic |
|---|---|---|---|
| 0.44 | $8 \times 10^{-5}$ | 8.0 | 237 |
| 0.27 | $6 \times 10^{-6}$ | 8.0 | 145 |
| 0.27 | $6 \times 10^{-6}{}_a$ | 8.2 | 117 |
| 0.28 | $5 \times 10^{-6}{}_b$ | 8.7 | 66 |
| 0.21 | $8 \times 10^{-6}{}_c$ | 9.3 | 20 |
| 0.14 | $1 \times 10^{-5}{}_d$ | 9.0 | 32 |
| 0.25 | $8 \times 10^{-6}{}_e$ | 8.2 | 10 |

Figure 1:
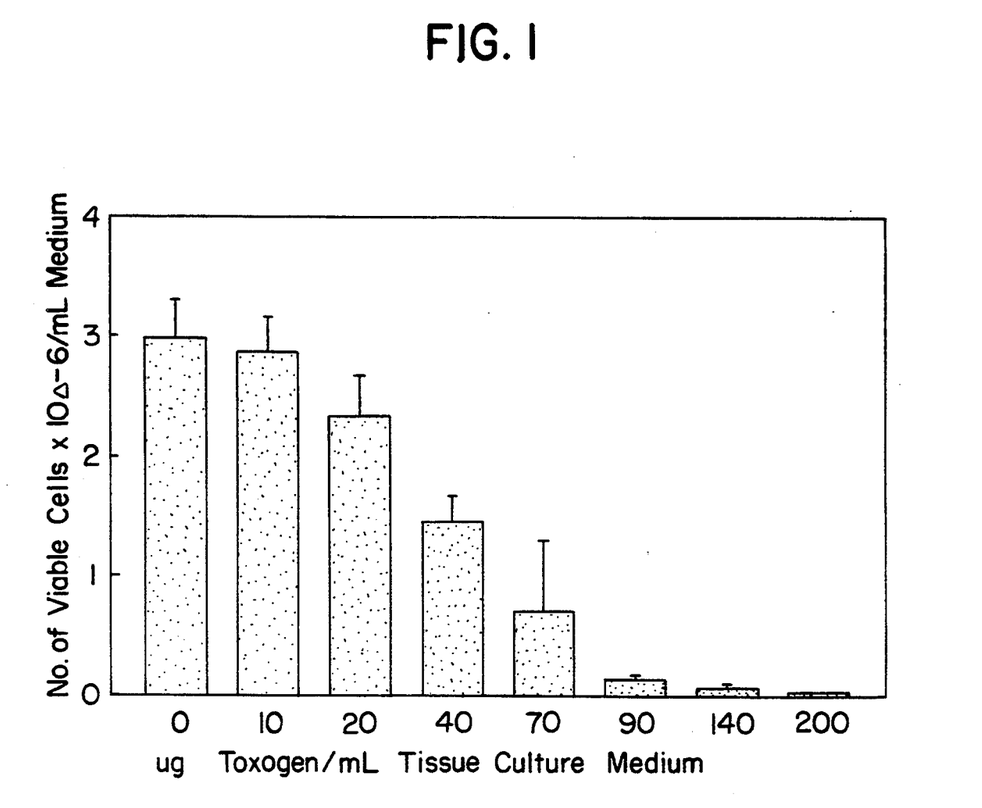
FIG. 1. Cytotoxic effect of the transferrin-gum arabic-araC conjugate on CCRF-CEM cells. CCRF-CEM cells were treated with various concentrations between 2 and 200 $\mu g/ml$ of the toxogen for 72 hours. Data points represent the composite of 3 experiments with duplicate cultures in each.
Figure 2A:
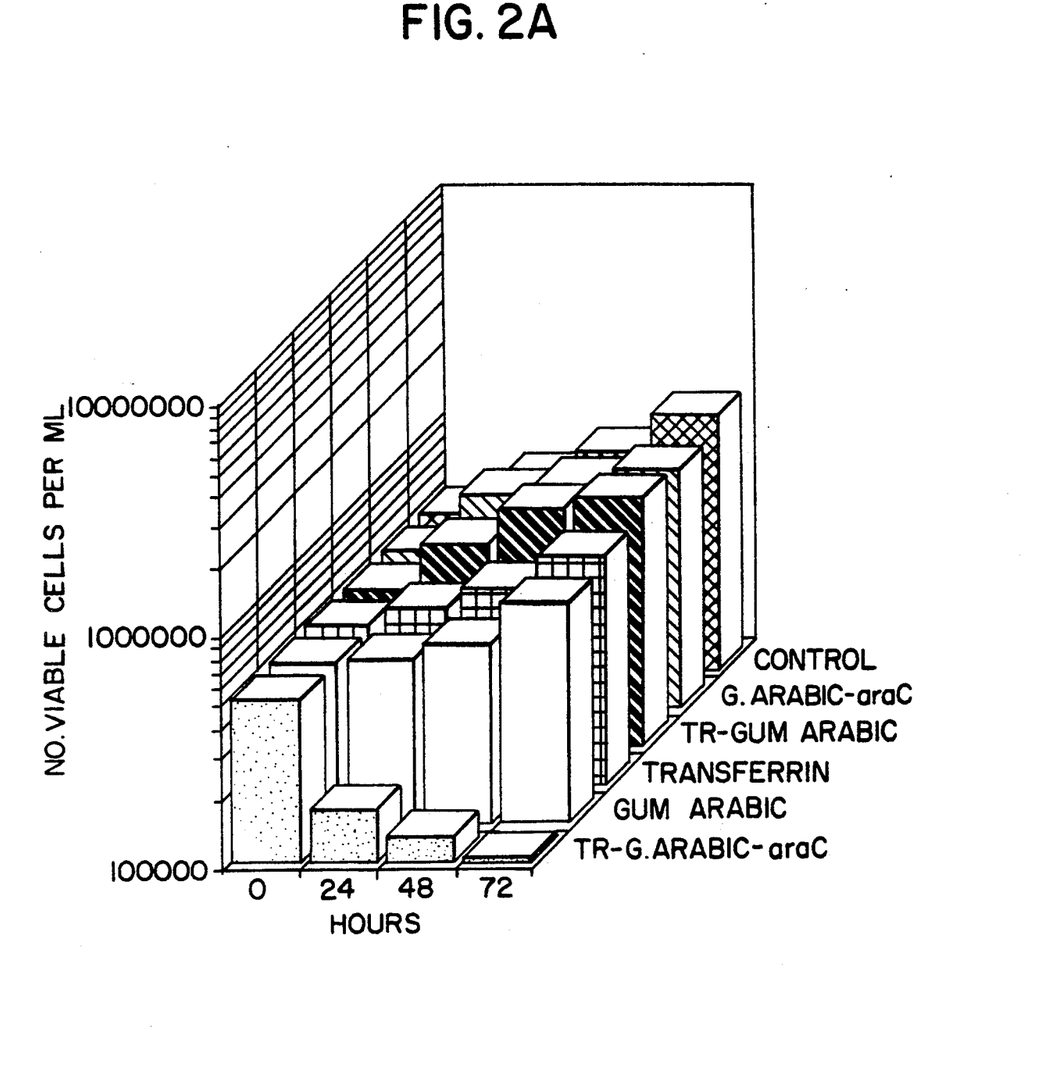
FIG. 2A. The effect of the transferrin-gum arabic-araC conjugate (200 $\mu g/ml$) on the growth and viability of CCRF-CEM cells. CCRF-CEM cells ($5 \times 10^5$ cells/ml) were treated with the toxogen or various components as controls. Amounts of components containing araC were added to keep the amount of araC constant (transferrin-gum arabic-araC, 200 $\mu g/ml$, transferrin, 200 $\mu g/ml$, gum arabic, 200 $\mu g/ml$, transferrin-gum arabic, 200 $\mu g/ml$, gum arabic-araC, 52 $\mu g/ml$). Data points represent the average of triplicate cultures. The experiment has been done 3 times with similar results. (Average Standard Deviation was $\pm 0.253$.)
Figure 2B:
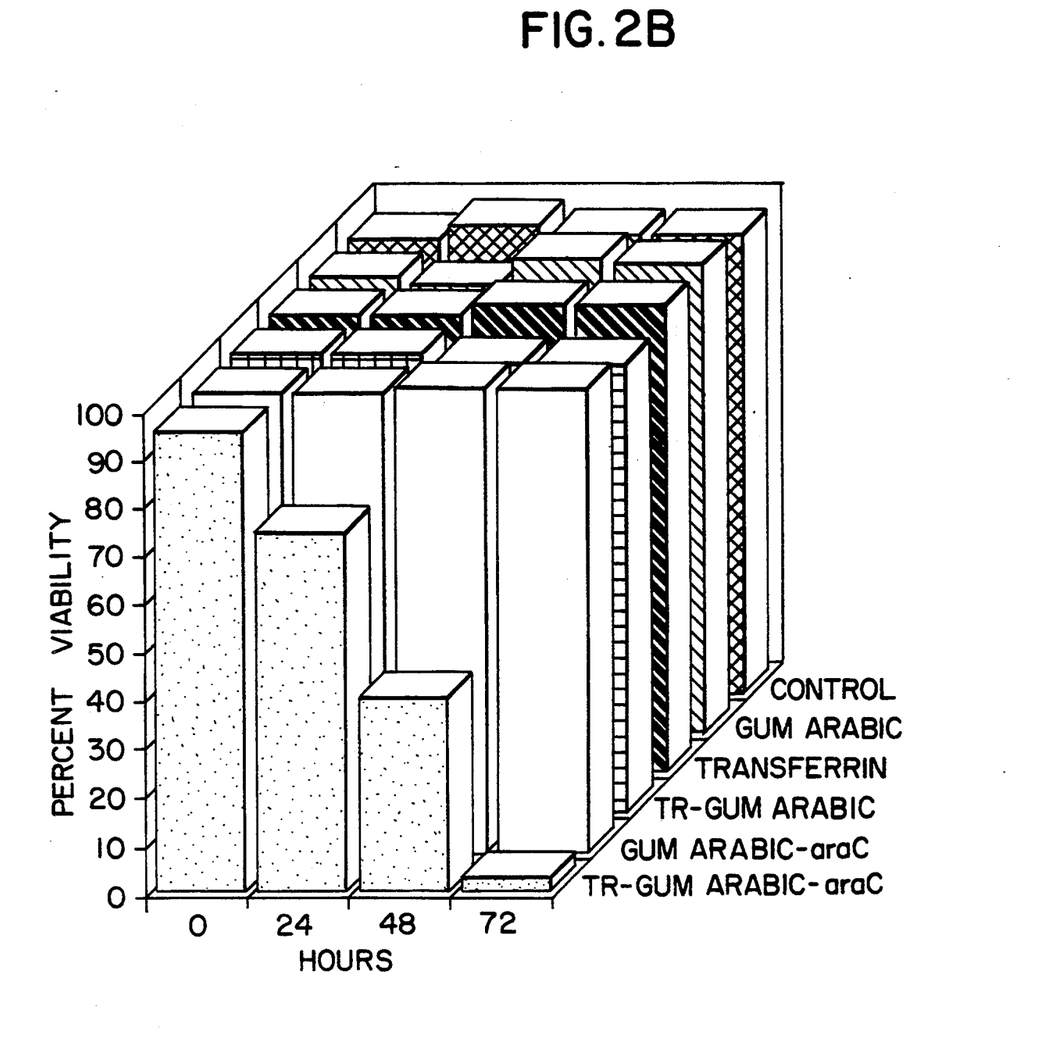
FIG. 2B. The effect of the transferrin-gum arabic-araC conjugate (200 $\mu g/ml$) on the growth and viability of CCRF-CEM cells. The viability of cells following exposure to the toxogen or one of the components of the toxogen as a control, (transferrin-gum arabic-araC, 200 $\mu g/ml$, transferrin, 200 g/mi, gum arabic, 200 $\mu g/ml$, transferrin-gum arabic, 200 $\mu g/ml$, gum arabic-araC, 52 $\mu g/ml$). Data points represent the average of triplicate cultures. The experiment has been done 3 times with similar results. (Average standard deviation was $\pm 0.271$.)

The polysaccharide was oxidized with 0.01 M sodium periodate for 48 hours at room temperature under dark conditions at pH 4.5 or:
$_a$with 0.1 M periodate at 4° C. for 48 hr in dark conditions at pH 4.5
$_b$with 0.2 M periodate at 4° C. for 48 hr in dark conditions at pH 4.5
$_c$with 0.01 M periodate at r.t. for 4.0 hr in dark conditions at pH 6.0
$_d$with 0.01 M periodate at r.t. for 2.0 hr in dark conditions at pH 6.0
$_e$with 0.005 M periodate at r.t. for 1.0 hr in dark conditions at pH 6.0 incubated with various concentrations of the toxogen over a period of 72 hours. FIG. (1) shows that the toxogen effectively inhibits the growth of tumor cells in a dose dependent manner. Two hundred μg/ml of the toxogen of the invention completely inhibited cell growth in 72 hours (FIG. 2A). Control cultures that received no treatment showed continued growth with 97% viability (FIG. 2B). Cells treated with the same amount of gum arabic-araC (alone) also showed continued growth with high viability as did cells treated with transferrin (alone) or gum arabic (alone) (FIG. 2A and FIG. 2B). Free araC at the concentration provided by the drug-conjugates showed similar inhibition to the toxogen.

EXAMPLE 3

Figure 3:
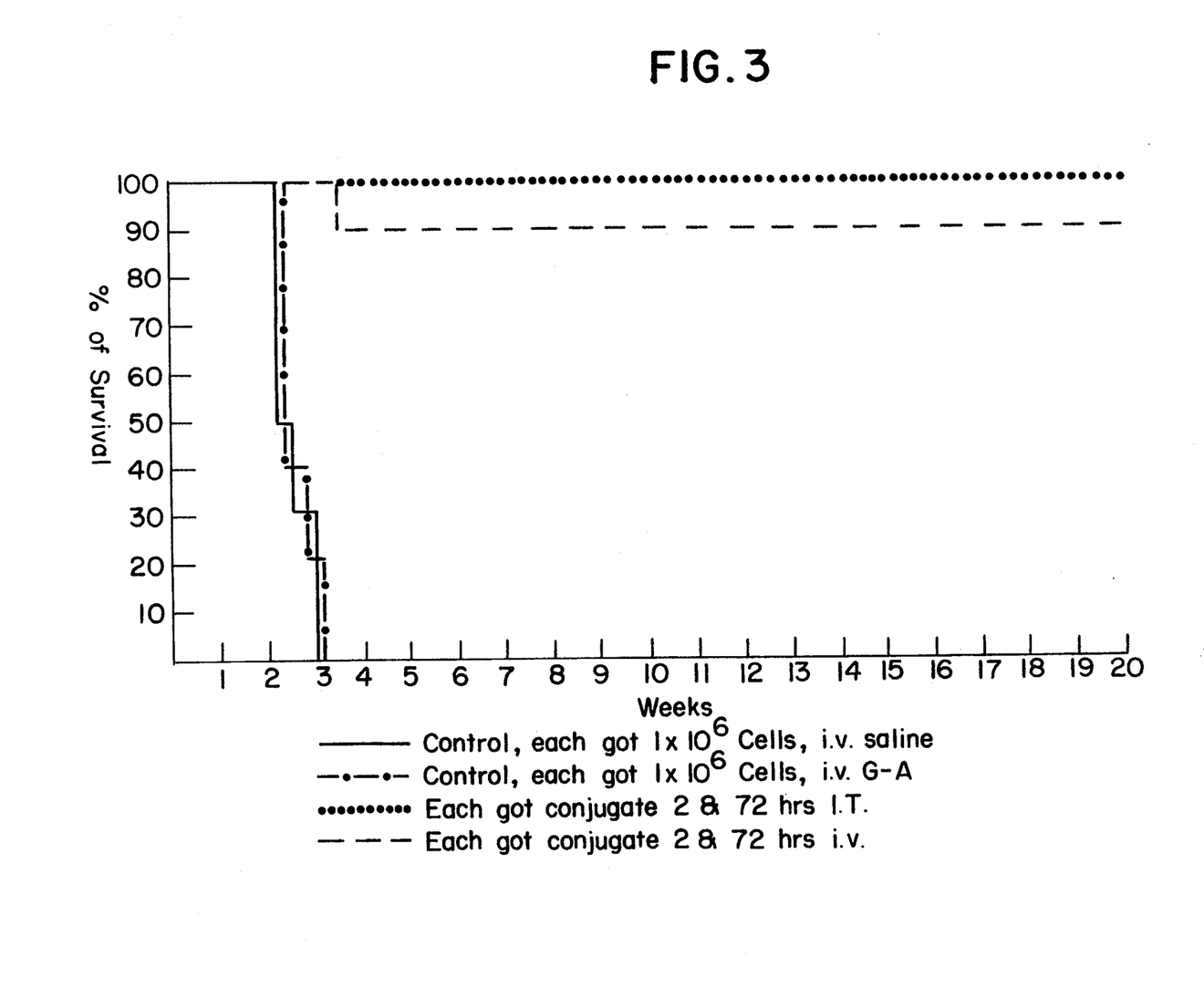
FIG. 3. Inhibition of SL-2 T-cell leukemia in AKR mice that have been treated with the transferrin-gum arabic-araC conjugate. Mice were treated with 0.5 mg of the toxogen (approximately 2.5 mg of araC/Kg) either intravenously or intratumorally 2 hours and 72 hours after receiving $1 \times 10^6$ tumor cells subcutaneously the flank. Control mice either received saline or 0.5 mg gum arabic-araC instead of the toxogen intravenously.
Figure 4A:
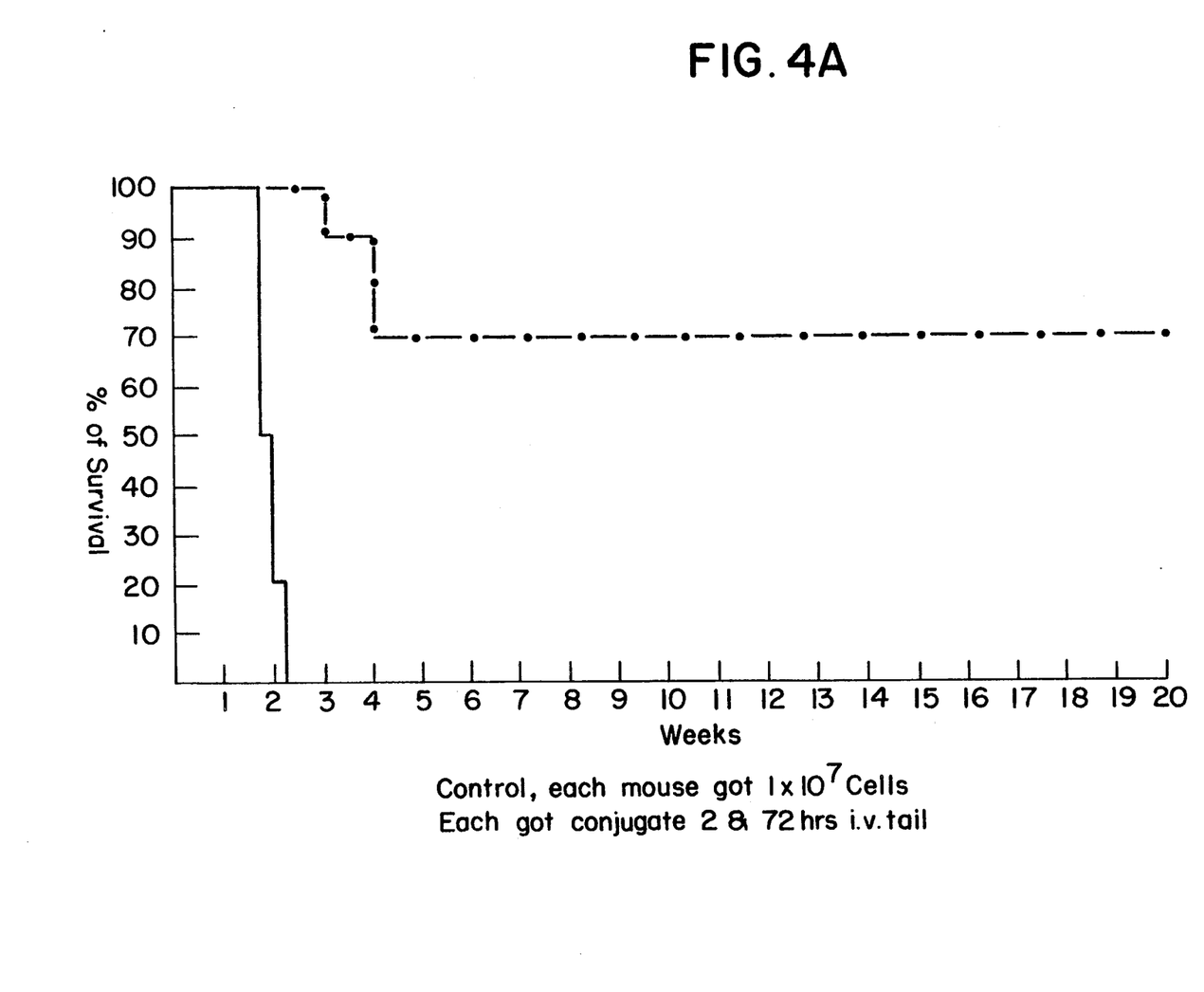
FIG. 4A. AKR mice transplanted with $1 \times 10^7$ SL-2 tumor cells and treated with 0.5 mg of the toxogen (approximately 2.5 mg of araC/Kg) 2 and 72 hours after tumor injection. Control mice received i.v. injection of saline instead of the toxogen.

Inhibition of T-cell leukemia growth in AKR mice: Since the transferrin-gum arabic-araC conjugates were effective cytotoxic agents in vitro, they were evaluated in vivo using SL-2 T-cell leukemia that has been shown to express a receptor for transferrin. AKR mice were inoculated subcutaneously with $1 \times 10^6$ or $1 \times 10^7$ SL-2 T-leukemic cells. Four groups of mice (10 mice each), were inoculated with $1 \times 10^6$ tumor cells, a dose 100-fold greater than that required to achieve tumor growth in 100% of the mice injected. One group was left untreated, two groups were given the transferrin-gum arabic-araC drug conjugate as prepared in Example 1(B) intravenously or intratumorally, and one control group received a gum arabic-araC conjugate intravenously. Mice treated with 0.5 mg of the transferrin-gum arabic-araC conjugate twice intravenously showed a 90% inhibition of tumor growth, while the same doses within the tumor completely prevented the growth of the T-cell leukemia (FIG. 3). The gum arabic-araC conjugate control failed to provide any protection and showed the same end point as untreated controls (FIG. 3). Mice transplanted with $1 \times 10^7$ cells and treated with 0.5 mg of the toxogen of the invention twice showed 70% inhibition of tumor growth (FIG. 4A).

EXAMPLE 4

Figure 4B:
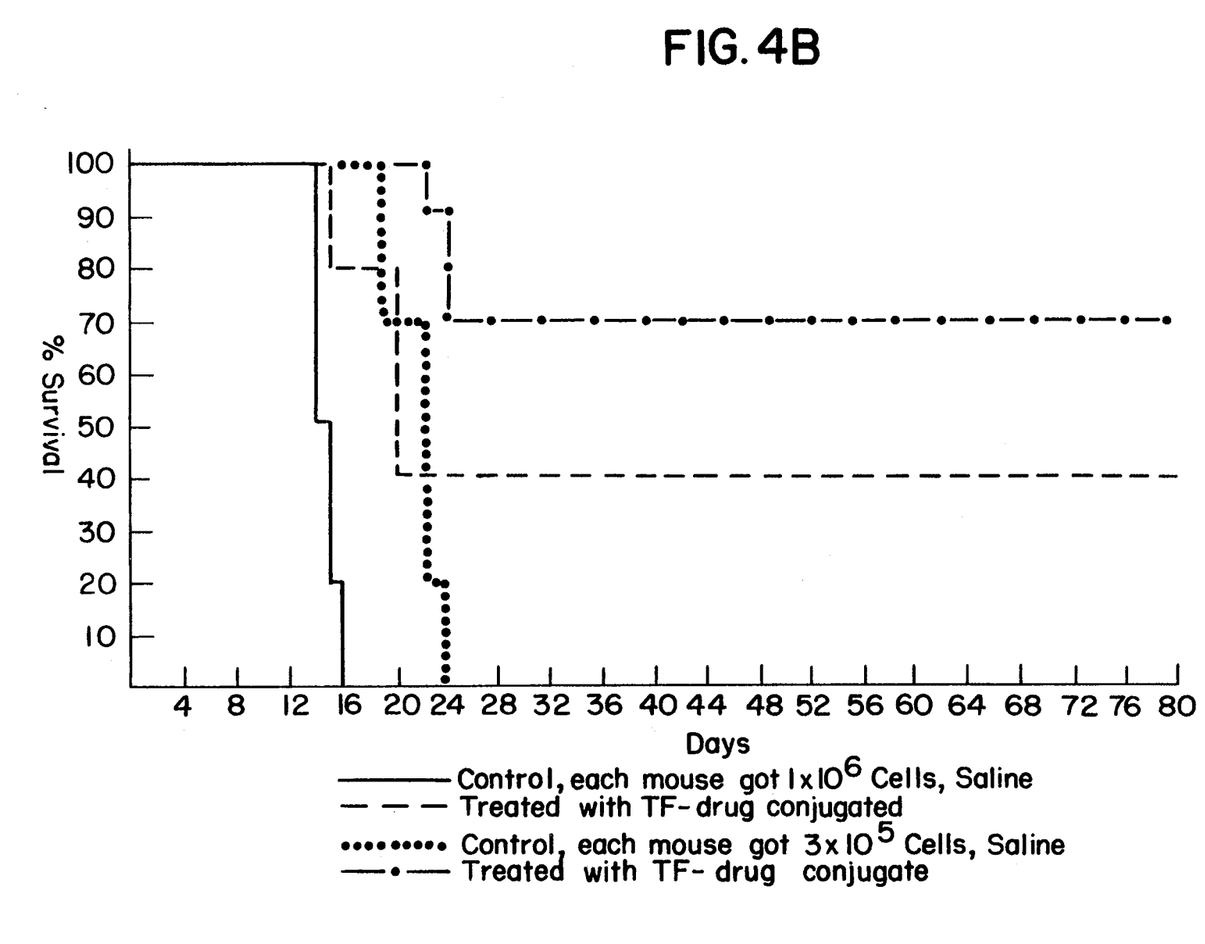
FIG. 4B. Regression of SL-2 T-cell leukemia in AKR mice treated with the transferrin-gum arabic-araC conjugate. Mice that received either $1 \times 10^6$ or $3 \times 10^5$ tumor cells were treated with 0.5 mg of the toxogen (approximately 2.5 mg of araC/kg) on seven consecutive days beginning with the third day following tumor implantation. Control mice received an equal volume of saline.
Figure 5A:
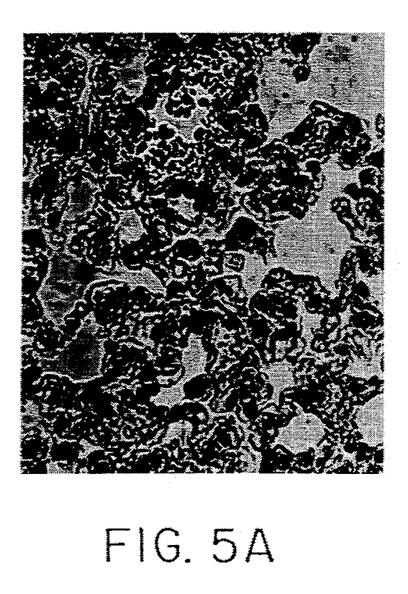
FIG. 5A through 5H. Histological evaluation of toxogen treated T-cell leukemia in the lung and liver following subcutaneous injection of $1 \times 10^6$ SL-2 T-cells in the flank. Incorporated bromouracil (to identify metastasizing lymphocytes) was detected by immunoperoxidase-anti-BUdR protocol. The tissue has been counterstained with hematoxylin. Two and 72 hours after implantation mice had received 0.5 mg of the toxogen (approximately 2.5 mg araC/Kg) per injection. 5A. Lung one day after tumor implantation with no toxogen treatment. 5B. Lung six days after tumor implantation with toxogen treatment. 5C. Lung eleven days after tumor implantation with toxogen treatment. 5D. Lung twelve days after tumor implantation with no toxogen treatment. 5E. Liver one day after tumor implantation with no toxogen treatment. 5F. Liver one day after tumor implantation with toxogen treatment. 5G. Liver eleven days after tumor implantation with toxogen treatment. 5H. Liver twelve days after tumor implantation with no toxogen treatment.
Figure 5B:
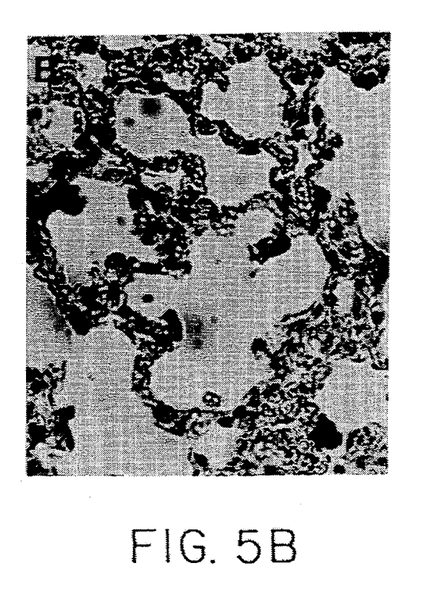
Figure 5C:
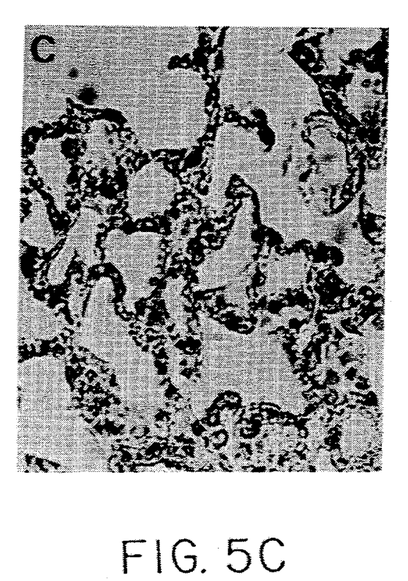
Figure 5D:
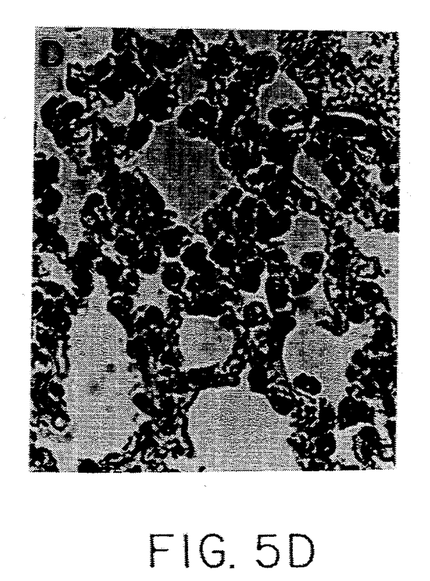
Figure 5E:
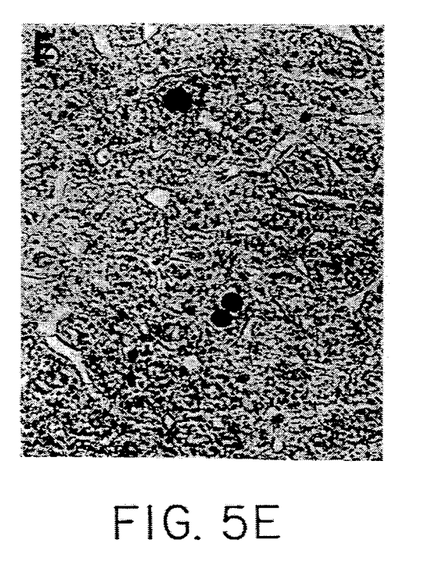
Figure 5F:
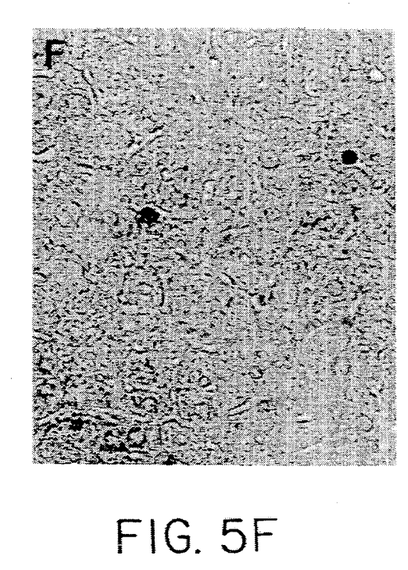
Figure 5G:
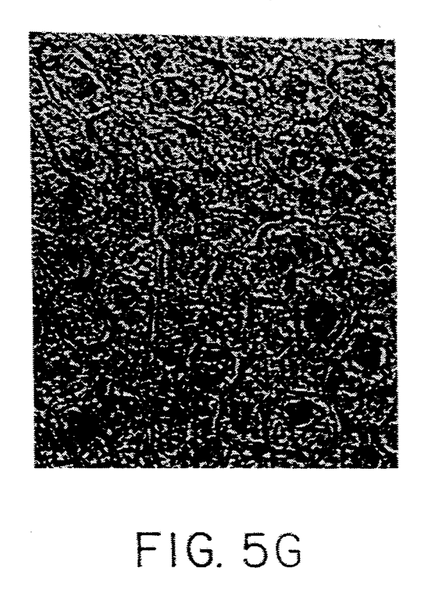
Figure 5H:
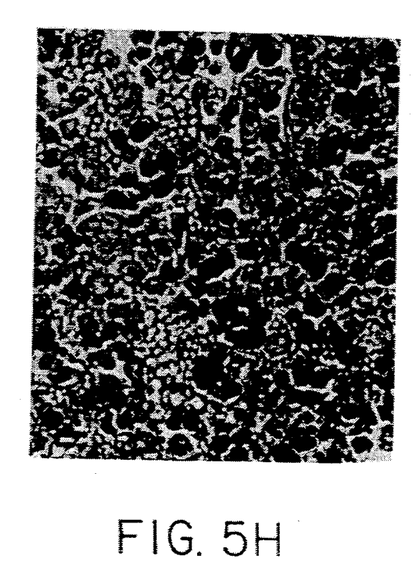

To evaluate whether therapy could still be effective after extensive engraftment of the leukemia cells, two groups of mice were challenged subcutaneously with $1 \times 10^6$ SL-2 leukemia cells and treated with transferrin-gum arabic-araC drug conjugate prepared as in Example 1(B), 72 and 96 hours later. The results demonstrated that a significant proportion of mice (40%) could be cured. To determine if more aggressive therapy might be more effective after extensive engraftment, mice that received $1 \times 10^6$ SL-2 leukemia cells were treated intravenously every day after the third day for seven consecutive days at a dose of 0.5 mg per day. The more aggressive therapy provided no additional improvement as still only 40% of the mice were long term survivors (FIG. 4B). However, with a reduced initial tumor burden, treatment with this aggressive protocol following extensive engraftment showed effective therapy with 70% long term survivors (FIG. 4B).

EXAMPLE 5

Immunohistochemical evaluation of tumor growth: Histological examination was used to identify proliferating cells in the livers, lungs and spleens from mice engrafted with either $1 \times 10^6$ or $3 \times 10^5$ tumor cells and treated with BUdR. Livers and lungs from mice engrafted with $1 \times 10^6$ cells were infiltrated with tumor cells as early as 24 hours after transplantation (FIG. 5). Mice that received $3 \times 10^5$ SL-2 leukemia cells showed infiltration of the liver and lung within 48 hours of tumor inoculation. In mice that received $1 \times 10^6$ leukemia cells and then were treated with the toxogen or conjugate as prepared in Example 1B, 2 hours as well as 72 hours later, histological examination of the spleens, livers and lungs following a BUdR infusion showed significant infiltration on the first day that decreased on successive days as a result of therapy. Mice that appeared to be cured by the toxogen treatment showed no signs of tumor infiltration and no signs of tissue damage 12 days after the therapy (FIG. 5).

EXAMPLE 6

Long term effects in toxogen treated animals: Mice that showed no signs of T cell leukemia six months after treatment with the toxogen as prepared in Example 1(B) were rechallenged with $3 \times 10^5$ SL-2 tumor cells. All mice developed tumors within 3 weeks; a time course that was identical to untreated animals. This indicates that the eradication of the tumor in treated animals was due to the toxogen and that there does not appear to be an immunological contribution to the tumor rejection.

EXAMPLE 7

To 1.0 ml (5.0 mg/ml) of oxidized gum arabic in citratephosphate buffer, 1.5 ml of EGF (epidemial growth factor) (20.0 μg/ml) were added, and the pH of the solution was maintained at 8.0 with NaOH. After the mixture was stirred for 15 minutes at room temperature, 3.0 ml (100.0 mg/ml) of araC trace labeled with $^3$H-araC were added to the oxidized polysaccharide, and the pH of the reaction mixture was adjusted to pH 8.0. Tritiated araC was used to calculate the number of drug molecules that were attached to the gum arabic component. The reaction was allowed to continue for two hours at room temperature while maintaining the pH at 8.0. Reactants were reduced with 2.0 M sodium borohydride (0.075 gm in 1.0 ml distilled water) for one hour at room temperature. The uncoupled reaction products were removed by overnight dialysis against borated buffered saline (BBS) at pH 8.0. The toxogen EGF-gum arabic-araC was stored at 4° C. In general, the number of araC molecules that were attached to the polysaccharide was in the range of about 150 or 2000. Based on the extinction coefficient for EGF ($E^{1\%}{}_{280}=30.9$) it was calculated that 2-3 EGF molecules were attached to each unit of carbohydrate.

EXAMPLE 8

Figure 6:
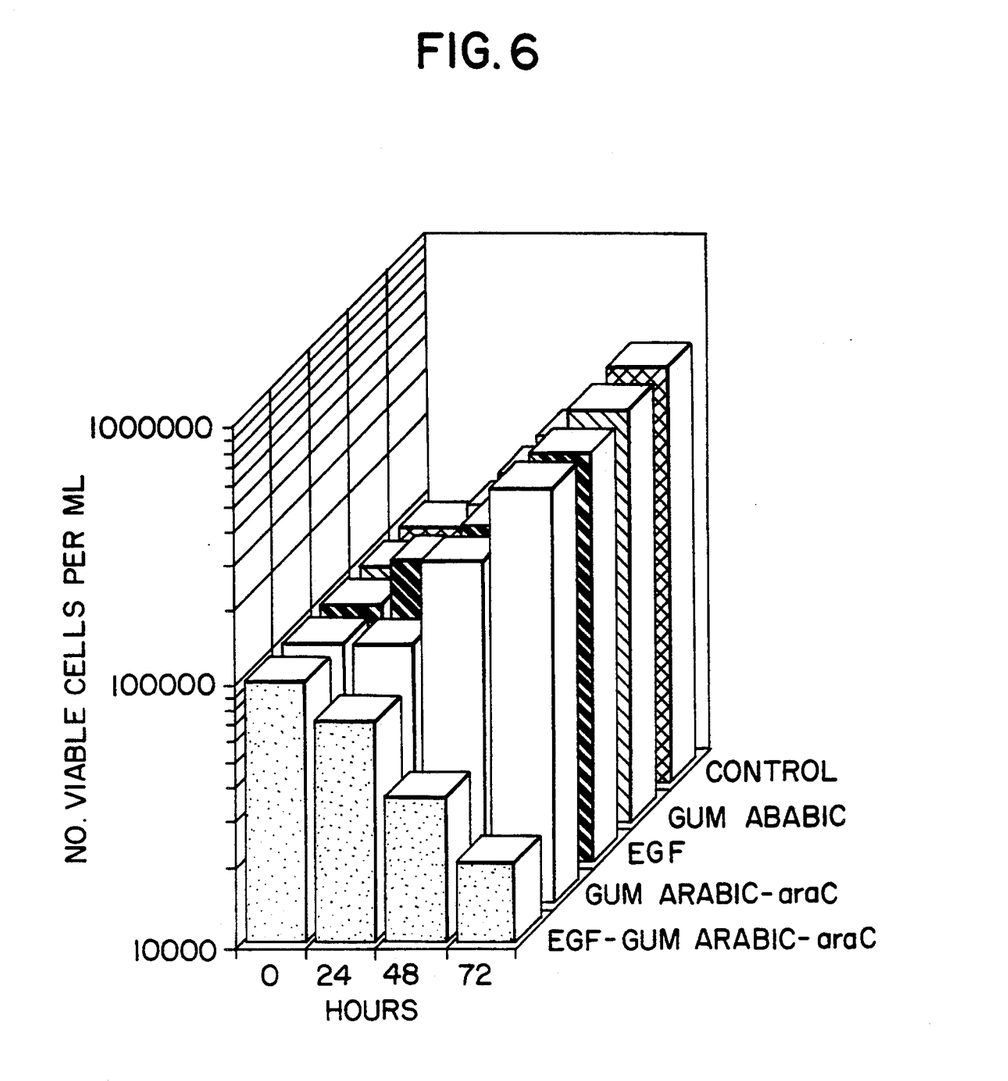
FIG. 6. The effect of EGF-gum arabic-araC conjugate on the growth of colon-26 tumor cells. Colon-26 cells ($2\times10^4$ cells/ml) were treated with the toxogen or various components as controls. Amounts of components containing araC were added to keep the amount of araC constant (EGF-gum arabic-araC, 60 µg/ml ; EGF, 5.0 µg/ml ; gum arabic, 60 µg/ml ; gum arabic-araC, 60 µg/ml ). Data points represent the average of duplicate cultures. The experiment has been done twice with similar results. (Average mean was +0.37.)
Figure 7:
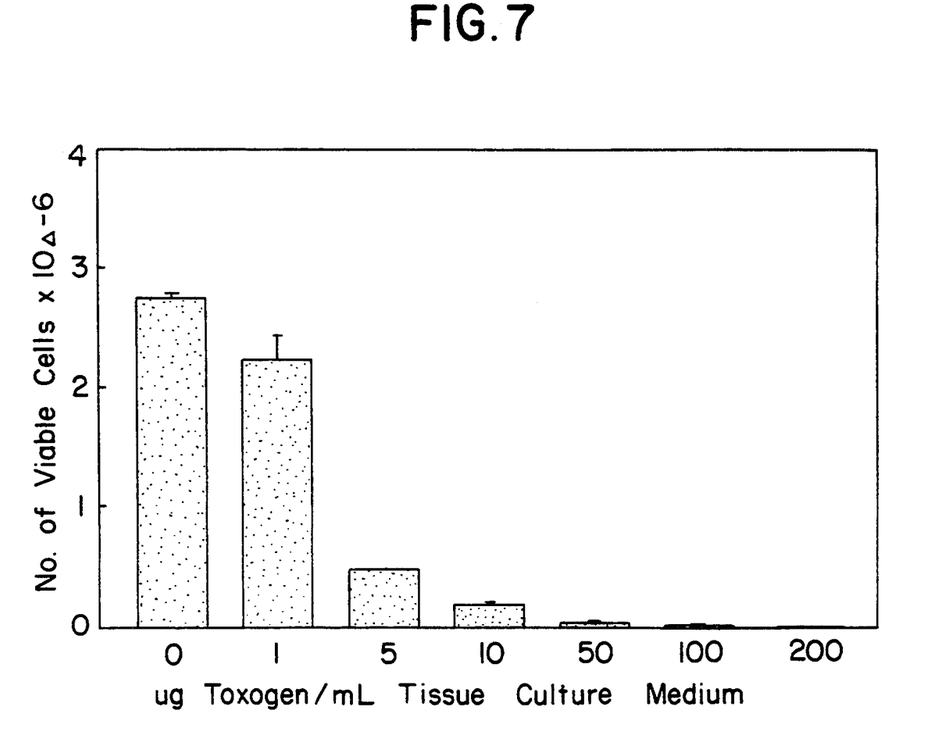
FIG. 7. Dose-response curve for colon-26 cells treated with 1 to 200 µg of the toxogen/ml of tissue culture for 72 hours. Data points represent the mean of triplicate cultures. A second experiment gave similar results.
Figure 8:
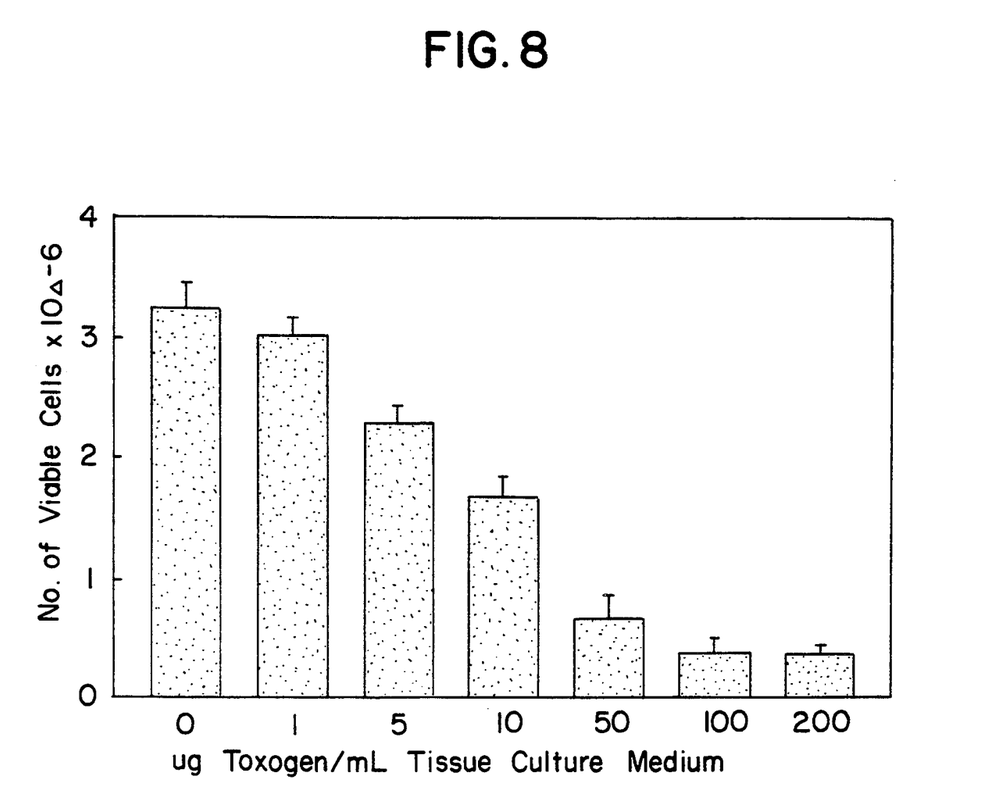
FIG. 8. Dose-response curve for C3H/10T$\frac{1}{2}$cells treated with 1 to 200 µg of toxogen/ml of tissue culture medium for a period of 72 hours. Data points represent the composite of two experiments done in duplicate.

In vitro cytotoxicity of epidermal growth factor-gum arabic-araC conjugate: Five ml of cells (colon-26 or C3H/10T½), $2 \times 10^4$ cells/ml were treated with various concentrations of the toxogen as prepared in Example 7 for 72 hours. The effect of the toxogen on the cell populations was determined from a cell count using trypan blue exclusion. The EGF- gum arabic-araC conjugate was tested on mouse colon-26 carcinoma cells. Tumor cells were incubated with various concentrations of the toxogen over a period of 72 hours. Sixty μg of the toxogen/ml of tissue culture medium completely inhibited cell growth in 72 hours when compared to control cultures that did not receive any treatment (FIG. 6). Cells treated with the same amount of gum arabic-araC (alone) also showed continued growth with high viability as did cells treated with EGF (alone) or gum arabic (alone) (FIG. 6). FIG. 7 shows that the toxogen at concentrations between 1 and 200 μg/ml culture medium effectively inhibits the growth of tumor cells in a dose dependent manner. Mouse fibroblasts (C3H/10T½) that express EGF receptors were also incubated with different concentrations of the EGF- gum arabic-araC conjugate of the invention. Two hundred μg/ml of the toxogen of the invention resulted in 89% growth inhibition and the toxogen was effective in dose-dependent manner at a concentration between 1 and 200 μg/ml of culture medium (FIG. 8). Growth of cells treated with either gum arabic-araC (alone) or EGF (alone) did not differ from control untreated cells.

EXAMPLE 9

Figure 9:
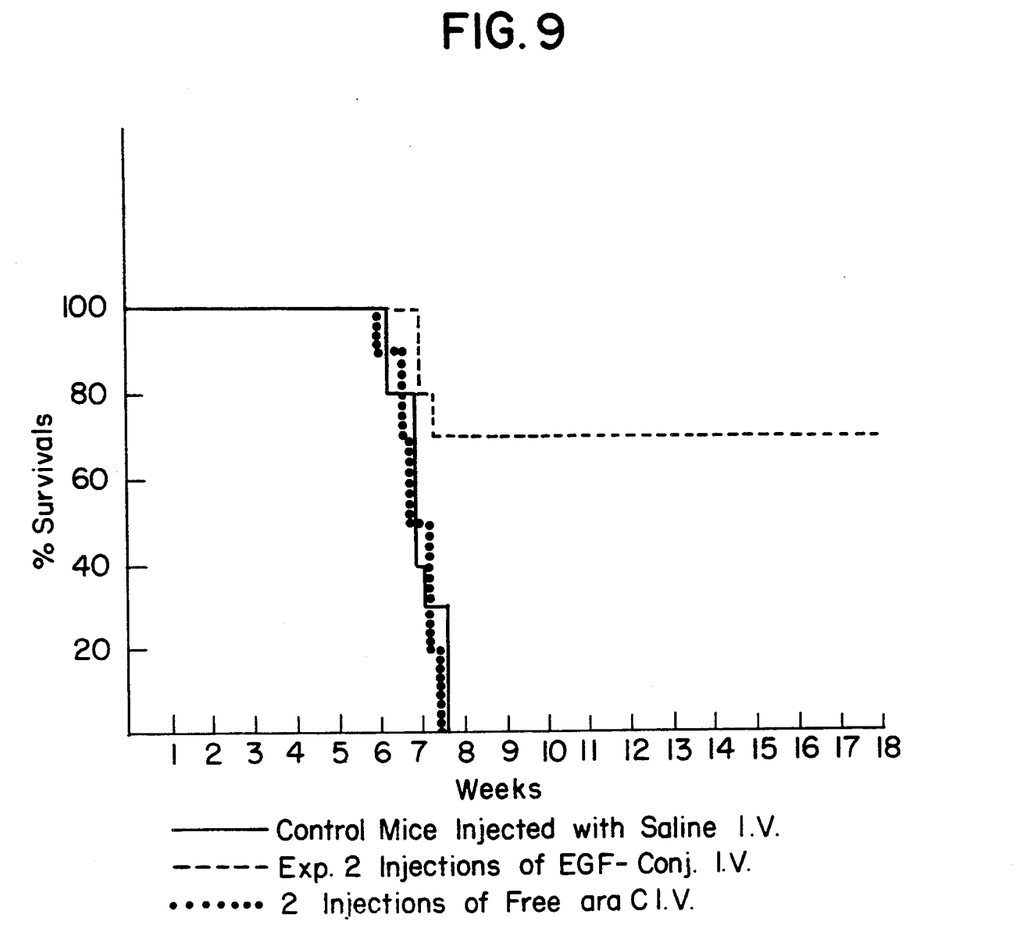
FIG. 9. BALB/c mice transplanted with $1\times10^6$ colon-26 tumor cells and treated with 0.13 mg of the toxogen (approximately 4.25 mg of araC/Kg) 2 and 72 hours after tumor injection. Control mice received i.v. injection of saline instead of the toxogen.

Inhibition of colon-26 tumor growth in BALB/c Mice: Mice were injected subcutaneously with $1 \times 10^6$ colon-26 cells, and then treated with the toxogen prepared as in Example 7 intravenously. Mice received 130.0 μg (0.2 ml) of the toxogen of the invention injected intravenously into the tail vein usually given 2 and 72 hours after injection of the tumor cells. Control groups of mice that received $1 \times 10^6$ tumor cells were injected intravenously with either free araC (equivalent to the toxogen) or saline. Preliminary studies showed that two intravenous injections of 0.13 mg of the EGF-gum arabic-araC toxogen (approximately 4.25 mg of araC/Kg), at 2 and 72 hours after tumor injection, prevented tumor growth in 70% of mice (FIG. 9). In addition, the administration of equivalent amounts of araC (approximately 100 μg/injection, 5.0 mg/Kg) had no effect on the growth of the tumor.

What is claimed is:

1. A composition of matter comprising a ligand-carbohydrate-cytotoxic drug conjugate wherein the carbohydrate has a molecular weight between 50,000 and 40 million and contains sufficient branching and sufficient adjacent hydroxyl group moieties such that at least 100 cytotoxic drug residues are attached to the carbohydrate.

2. The composition of matter of claim 1 wherein the ligand is a compound that can bind to a surface receptor of a cell.

3. The composition of claim 1 wherein the ligand is a cytokine.

4. The composition of claim 1 wherein the ligand is a growth factor.

5. The composition of claim 1 wherein the ligand is a natural ligand selected from transferrin, epidermal growth factor and GM-CSF.

6. The composition of claim 1 wherein the ligand is iron-saturated human transferrin.

7. The composition of claim 1 wherein the cytotoxic drug is selected from cytosine arabinoside (araC), melphalan, adriamycin and methotrexate.

8. The composition of claim 1 wherein the cytotoxic drug is a cytosine arabinoside ($^3$H)ara-C.

9. The composition of claim 1 wherein the carbohydrate is a polysaccharide.

10. The composition of claim 1 wherein the carbohydrate is highly branched.

11. The composition of claim 1 wherein the carbohydrate comprises about 250 to about 200,000 monomer units with cis diols or adjacent aminohydroxy groups.

12. The composition of claim 1 wherein the carbohydrate is capable of carrying about 100 to about 20,000 molecules of araC per mole of carbohydrate and withstanding fragmentation on oxidation with periodate.

13. A composition of matter of claim 1 comprising a tranferrin-gum arabic - cytosine arabinoside conjugate.

14. A composition of matter of claim 1 comprising an epidermical growth factor - gum arabic - cytosine arabinoside conjugate.

15. A process for producing a ligand-carbohydrate-cytotoxic drug conjugate of claim 1 comprising the steps of:
  (1) reacting a carbohydrate with a ligand,
  (2) reacting the product of step (1) with a cytotoxic drug, and
  (3) stabilizing the product of step (2) by reduction.

16. The process of claim 15 wherein the ligand is a compound that can bind to a surface receptor on a cell.

17. The process of claim 15 wherein the ligand is a cytokine.

18. The process of claim 15 wherein the ligand is a growth factor.

19. The process of claim 15 wherein the ligand is a natural ligand selected from transferrin, epidermal growth factor and GM-CSF.

20. The process of claim 19 wherein the natural ligand is iron-saturated human transferrin.

21. The process of claim 15 wherein the carbohydrate is a polysaccharide.

22. The process of claim 21 wherein the carbohydrate is an oxidized polysaccharide.

23. The process of claim 15 wherein the cytotoxic drug is selected from cytosine arabinoside (araC), melphalan, adriamycin and methotrexate.

24. The process of claim 15 wherein the cytotoxic drug is ($^3$H) ara-C.

25. The process of claim 23 wherein the carbohydrate is a polysaccharide.

26. The process of claim 25 wherein the polysaccharide is highly branched and oxidized.

27. The process of claim 15 wherein the polysaccharide comprises about 250 to about 200,000 monomer units with cis diols or adjacent amino hydroxyl groups.

28. The process of claim 15 that is capable of carrying about 100 to about 20,000 moles of araC per mole of carbohydrate and withstanding fragmentation on oxidation with periodate.

29. A process of claim 15 wherein the conjugate comprises a tranferrin-gum arabic - cytosine arabinoside conjugate.

30. A process of claim 15 wherein the conjugate comprises an epidermical growth factor - gum arabic - cytosine arabinoside conjugate.

31. A method for treating a neoplastic disease by a process of administering a non-toxic, effective amount of a ligand-carbohydrate-cytotoxic drug conjugate of claim 1 to a human being or animal in need of such a treatment.

32. The method of claim 31 wherein the neoplastic disease is selected from a leukemia, a carcinoma, a sarcoma, a melanoma and a mixed type of neoplasia.

33. The method of claim 31 wherein the ligand is a compound that can bind to a surface receptor on a cell.

34. The method of claim 31 where the ligand is a cytokine.

35. The method of claim 31 wherein the ligand is a growth factor.

36. The method of claim 31 wherein the ligand is a ligand selected from transferrin, epidermal growth factor and GM-CSF.

37. The method of claim 31 wherein the ligand is iron-saturated human transferrin.

38. The method of claim 31 wherein the cytotoxic drug is selected from cytosine arabinoside (araC), melphalan and adriamycin.

39. The method of claim 31 wherein the cytotoxic drug is ($^3$H) ara-C.

40. The method of claim 31 wherein the carbohydrate is a polysaccharide.

41. The method of claim 31 wherein the polysaccharide is highly branched.

42. The method of claim 31 wherein the polysaccharide comprises a number of monomer units with cis diols.

43. The method of claim 31 wherein the polysaccharide is capable of carrying about 100 to about 20,000 moles of araC per mole of polysaccharide molecules and withstanding fragmentation on oxidation with pariodate.

44. A method of claim 31 wherein the conjugate comprises a tranferrin-gum arabic - cytosine arabinoside conjugate.

45. A method of claim 31 wherein the conjugate comprises an epidermical growth factor - gum arabic - cytosine arabinoside conjugate.

46. The composition of claim 1 wherein from about 100 to about 2,000 moles of drug residue are present per mole of carbohydrate and the carbohydrate is oxidized.

47. The composition of claim 1 wherein the carbohydrate is gum arabic.

48. The composition of claim 47 wherein the gum arabic is oxidized.

* * * * *